United States Patent [19]

Lopez-Berestein et al.

[11] Patent Number: 4,812,312

[45] Date of Patent: Mar. 14, 1989

[54] LIPOSOME-INCORPORATED NYSTATIN

[75] Inventors: Gabriel Lopez-Berestein; Reeta Mehta; Roy L. Hopfer; Rudolph L. Juliano, all of Houston, Tex.

[73] Assignee: Board of Regents of the University of Texas System, Austin, Tex.

[21] Appl. No.: 21,367

[22] Filed: Mar. 3, 1987

[51] Int. Cl.$^4$ ............ A61K 37/22; A61K 37/00; A61J 5/00; B32B 5/16
[52] U.S. Cl. .................. 424/417; 264/4.1; 264/4.3; 264/4.6; 424/450; 428/402.2; 514/31
[58] Field of Search ............... 424/417, 450; 264/4.1, 264/4.3, 4.6; 428/402.2

[56] References Cited

U.S. PATENT DOCUMENTS

| | | | |
|---|---|---|---|
| 4,186,183 | 1/1980 | Steck et al. | 424/38 |
| 4,235,871 | 11/1980 | Papahadjopoulos et al. | 424/19 |
| 4,330,534 | 5/1982 | Sakurai et al. | 424/182 |
| 4,515,736 | 5/1985 | Deamer | 424/450 |

FOREIGN PATENT DOCUMENTS

WO87/01933  4/1987  World Int. Prop. O.

OTHER PUBLICATIONS

International Search Report for PCT/US 88/00632.
Iqbal, Z. et al., *Chem. Abstracts* (1979), 91, No. 15:426–435.
Cohen, B. E., *Chem. Abstracts* (1975), 83, No. 9:267.
New, R. R. C., "Antileishmanial Activity of Amphotericin and Other Antifungal Agents Entrapped in Liposomes", Journal of Antimicrobial Chemotherapy, 1981, pp. 371–381.
Tom, Baldwin, H., "An Overview: Liposomes and Immunobiology–Macrophages, Liposomes, and Tailored Immunity", 1980, Liposomes and Immunobiology, pp. 3–19.
The Merck Index, 10th Edition, Martha Windholz (ed.), Merck & Co., Inc., Rahway, N.J. (1983), p. 85, section 611.
The Merck Index, 10th Edition, Martha Windholz (ed.), Merck & Co., Inc., Rahway, N.J. (1983), p. 967, section 6580.
LEXIS/NEXIS Patent Search.
DIALOG Literature Search.
Chemical Abstracts, vol. 91, 1979, 102345n, p. 80.

(List continued on next page.)

*Primary Examiner*—Douglas W. Robinson
*Attorney, Agent, or Firm*—Arnold, White & Durkee

[57] ABSTRACT

The present invention involves a liposomal agent for treating disseminated fungal infection in an animal. This liposomal agent comprises the polyene antifungal compound nystatin. The nystatin is encapsulated within a liposome. The liposome in which the nystatin is incorporated is preferably a stable multilamellar vesicle. The liposome broadly comprises one or more lipids one or more of phosphomonoglyceride, phosphatidic acid and sphingolipid. The lipids are preferably one or more of phosphatidylcholine, phosphatidylserine, phosphatidylglycerol, sphingomyelin or phosphatidic acid. The lipids are most preferably one or more of dimyristoylphosphatidylcholine, dimyristoylphosphatidylglycerol, phosphatidylcholine and phosphatidylglycerol. The liposome of the present invention may comprise a sterol most preferably cholesterol. An important aspect of the present invention involves a method for treating disseminated fungal infection in an animal. This method comprises administering to an animal subject to disseminated fungal infection a fungicidally effective amount of nystatin encapsulated within a liposome. The liposome is composed as described above. The administering is preferably parenteral in most instances but may be oral or topical if specific colonies of fungus are thereby more directly reached. This treatment method is most useful when the animal is a human suffering from disseminated fungal infection. The method of treatment involves a fungicidally effective amount of liposome-incorporated nystatin of between about 1 mg nystatin/kg body weight and about 6 mg nystatin/kg body weight. In a most preferred embodiment the treatment method comprises liposomes consisting essentially of dimyristoylphosphatidylcholine and dimyristoylphosphatidylglycerol in a ratio of about 7:3.

13 Claims, 4 Drawing Sheets

OTHER PUBLICATIONS

Chemical Abstracts, vol. 92, 1980, 123748q, pp. 248-249.
Chemical Abstracts, vol. 92, 1980, 176122e, p. 208.
Chemical Abstracts, vol. 93, 1980, 127554j, p. 234.
Chemical Abstracts, vol. 95, 1981, 161822w, p. 33.
Chemical Abstracts, vol. 96, 1982, 57652a, p. 360.
Chemical Abstracts, vol. 84, 1976, 146551m, p. 205.
Chemical Abstracts, vol. 87, 1977, 80067m, p. 193.
Chemical Abstracts, vol. 87, 1977, 193716r, p. 40.
Chemical Abstracts, vol. 91, 1979, 104067x, p. 251.
Chemical Abstracts, vol. 93, 1980, 142742n, p. 32.
Chemical Abstracts, vol. 93, 1980, 198021u, p. 85.
Chemical Abstracts, vol. 93, 1980, 198503c, p. 141.
Chemical Abstracts, vol. 95, 1981, 37636z, p. 272.
Chemical Abstracts, vol. 95, 1981, 182480y, p. 219.
Chemical Abstracts, vol. 87, 1977, 195913b, p. 254.
Chemical Abstracts, vol. 89, 1978, 157215j, p. 23.
Chemical Abstracts, vol. 90, 1979, 163615b, p. 179.
Chemical Abstracts, vol. 90, 1979, 82569n, p. 206.
Abstracts of the 1983 ICAAC, p. 133.
Product Information, p. 1929, Physician's Desk Reference.
Chemical Abstracts, vol. 78, 1973, 53407e, pp. 106-107.
Chemical Abstracts, vol. 79, 1973, 27977s, p. 108.
Chemical Abstracts, vol. 79, 1973, 28102q, p. 119.
Chemical Abstracts, vol. 80, 1974, 23178e, pp. 80-81.
Chemical Abstracts, vol. 84, 1976, 100974y, p. 185.
Chemical Abstracts, vol. 87, 1977, 163184y, p. 177.
Magee, Wayne E. et al., "A Comparison of Negatively and Positively Charged Liposomes Containing Entrapped Polyinosinic Polycytidylic Acid for Interferon Induction in Mice", 451, Biochimica et Biophysica Acta, 1976, pp. 610-618.
Abstracts of the 1982 ICAAC, p. 152.
Abstracts of the 1983 ICAAC, p. 222.
Schassner et al., *Biochemical Pharmacology*, 35:4110-4113 (1986).
Lopez-Berestein, G. et al., "Effects of Sterols on the Therapeutic Efficacy of Liposomal Amphotericin B in Murine Candidiasis", vol. 1, No. 1, *Cancer Drug Delivery*, 1983, pp. 37-42.
Lopez-Berestein, G. et al., "Treatment and Prophylaxis of Disseminated Infection Due to Candida Albicans in Mice with Liposome-Encapsulated Amphotericin B", vol. 147, No. 5, *The Journal of Infectious Diseases*, May 1983, pp. 939-945.
Juliano, Rudy et al., "Pharmacokinetic and Therapeutic Consequences of Liposomal Drug Delivery: Fluorodeoxyuridine and Amphotericin B as Examples", vol. 47, *Biologie Cellularaire*, May 1983, pp. 39-46.
Hopfer, R. L., "In Vitro Antifungal Activities of Amphotericin B and Liposome-Encapsulated Amphotericin B", vol. 25, No. 3, Antimicrobial Agents and Chemotherapy, Mar. 1984, pp. 387-389.
Mehta, R. et al., "Liposomal Amphotericin B is Toxic to Fungal Cells but not to Mammalian Cells", Biochimica et Biophysica Acta, 770 (1984), pp. 230-234.
Lopez-Berestein, Gabriel et al., "Altered Tissue Distribution of Amphotericin B by Liposomal Encapsulation: Comparison of Normal Mice to Mice Infected with Candida Albicans", vol. 1, No. 3, Cancer Drug Delivery, Jun. 1984, pp. 199-205.
Lopez-Berestein, Gabriel et al., "A Preliminary Communication: Treatment of Systemic Fungal Infections in Cancer Patients with Liposome Encapsulated-Amphotericin B".
Lopez-Berestein, Gabriel et al., "Prophylaxis of Candida Albicans Infection in Neutropenic Mice with Liposome-Encapsulated Amphotericin B", vol. 25, No. 3, Antimicrobial Agents and Chemotherapy, Mar. 1984, pp. 366-367.
Lopez-Berestein, G. et al., "Treatment with Liposome-Encapsulated Amphotericin B of Disseminated Candidiasis in Neutropenic Mice".
Graybill, John R. et al., "Treatment of Murine Cryptococcosis with Liposome-Associated Amphotericin B", vol. 145, No. 5, The Journal of Infectious Diseases, May 1982, pp. 748-752.
Taylor, Robert L., "Amphotericin B in Liposomes: A Novel Therapy for Histoplasmosis".

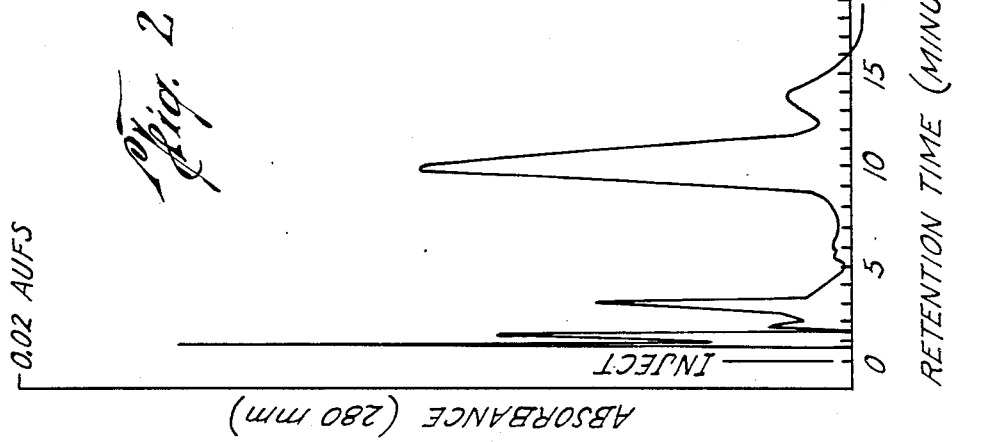
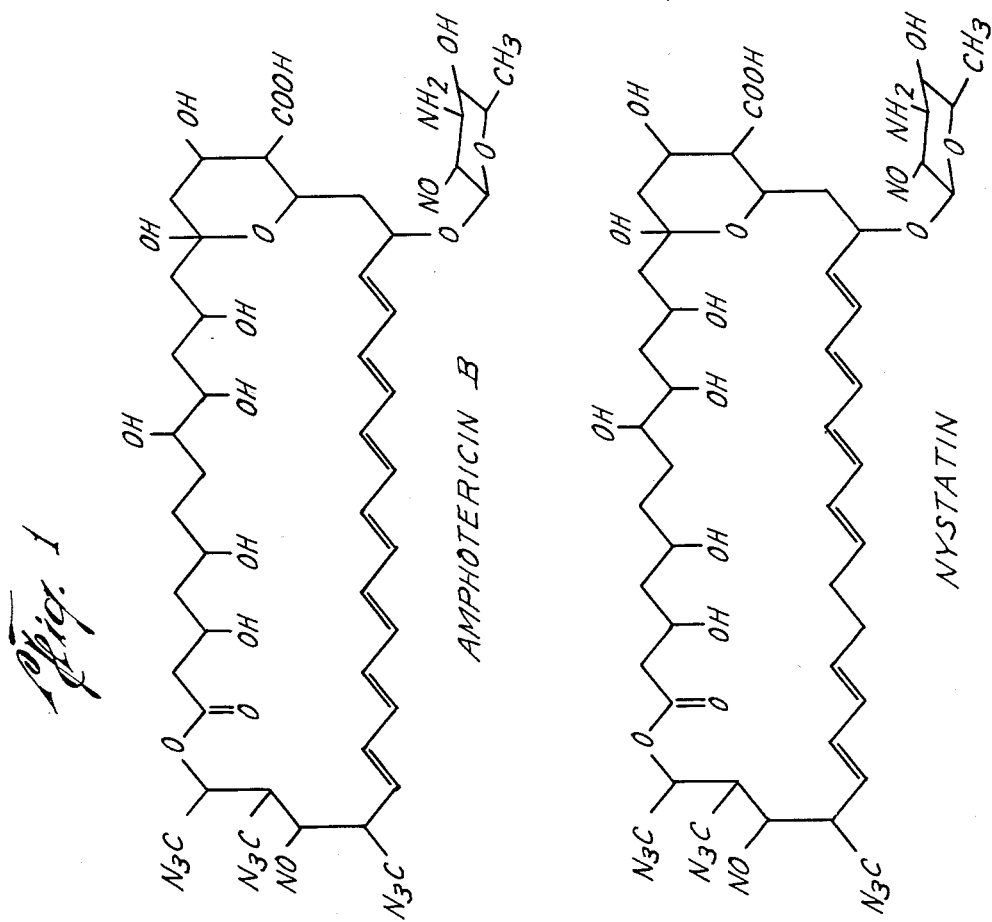

LIPOSOME-INCORPORATED NYSTATIN

BACKGROUND OF THE INVENTION

The development of part of the present invention was supported by contract number NIAID-NO1-AI42547 from the National Institutes of Health, Department of Health and Human Services.

The present invention relates to the treatment of systemic fungal infections by administration of liposome-incorporated nystatin.

Clinical observations and animal experimental studies have added to the understanding of host-fungal interactions. It is becoming recognized that host defense against fungal disease is multifactorial and may vary, depending on the etiologic agent. The mechanisms of resistance are not well defined in most instances, but various innate barriers and cell-mediated immune responses seem to be of primary importance. At this time, the role of antibody in resistance is uncertain. Clearly, debilitation of innate defenses and of cell-mediated immune responses can increase an individual's susceptibility to severe fungal disease from opportunistic agents such as *Cryptococcus neoformans* and species of Candida and Aspergillus, as well as from fungal pathogens such as *Histoplasma capsulatum* and *Coccidioides immitis*. The difficulty in gaining a complete understanding of the critical host defenses has been further complicated by many studies that show fungi may affect various host immune functions adversely. Although it is too early to evaluate the clinical importance of many of these experimental findings, investigators have demonstrated that fungi impair neutrophil function, induce IgE responses, and cause suppression of cell-mediated immune responses.

Host changes likely to be associated with increased susceptibility may be accidentally induced, as in traumatic injuries (such as burns or puncture wounds); self-induced, as in chronic alcoholism; naturally occurring, as in diabetes mellitus, various congenital immune deficiencies, collagen diseases, lymphoreticular neoplastic disease, and other types of tumors; or iatrogenically induced by instrumentation (such as catheterization), surgical procedures (such as open heart surgery), or by use of cytotoxic drugs (as in an attempt to prevent graft rejection and to treat neoplastic disease), corticosteroid therapy, and long-term use of broad-spectrum antibodies.

Chemical factors that aid resistance to fungal diseases are poorly defined. Knowledge of these substances is based primarily on circumstantial evidence at the clinical level and in vitro observations at the experimental level. Hormonally associated increases in lipid and fatty acid content on the skin occurring at puberty have been correlated with increased resistance to tinea capitis caused by the dermatophyte *Microsporum audouinii*, although pubescent changes are not the sole factors in resistance. Substances in serum, cerebrospinal fluid, and saliva may limit growth of *Cryptococcus neoformans*, and basic peptides in body fluids have been shown to inhibit *Candida albicans*.

Results of clinical and experimental studies indicate that *C. albicans, C. neoformans, Aspergillus fumigatus,* and *C. immitis* activate the alternative pathway of the complement cascade. Because of the polysaccharide nature of fungal cell walls, it is expected that all medically important fungi activate complement. Such activation may be important in defense against some mycoses; a positive correlation has been demonstrated between animals deficient in late-acting complement components (C3–C9) and increased susceptibility to fungi such as *C. neoformans* and *C. albicans*. Assuming that phagocytic cells are important in resistance to fungi, complement activation may play a role by provoking an acute inflammatory response on generation of complement fragments C3a and C5a, and by coating the fungal elements with opsonic fragments C3b and C3d for ingestion by phagocytic cells.

The systemic mycoses of humans and other animals are caused by some fungi that are pathogenic and cause disease in the healthy host, and by other fungi (opportunistic pathogens) that are usually innocuous but cause disease in patients whose immune defenses are impaired. Some of these fungi may be saprophytes in nature (soil, bird droppings), whereas others are a part of the normal human flora (commensals). In no case are humans the solitary or necessary host.

An example of a soil saprophyte is *Histoplasma capsulatum*, which commonly causes infection in endemic areas; 80%–90% of adults react positively to histoplasmin in delayed cutaneous hypersensitivity tests. An example of an opportunistic pathogen is *Candida albicans*, normally present in the oral cavity, gastrointestinal tract, and probably the skin. In the patient with acute leukemia, however, *C. albicans* is commonly present in blood, causing a fulminant, usually fatal, septicemia. Other opportunistic infections are seen in patients with diabetic acidosis (mucormycosis) and Hodgkin's disease (for example, cryptococcosis and histoplasmosis). The pathogenesis of these mechanisms is obscure, but cell-mediated immunity seems to be essential for a good prognosis.

Neither active vaccines nor passive immune serum immunization has been sufficiently successful to result in commercially available preparations.

Treatment of active disease may be symptomatic (for example, pain relief), sometimes surgical (resection of irremediably damaged tissue and correction of hydrocephalus), and, most successfully, chemotherapeutic (Table 1). Among the agents commonly used are hydroxystilbamidine isethionate, amphotericin B, 5-fluorocytosine (Flucytosine), miconazole, and ketoconazole. Response to these drugs varies according to the fungus, type of disease, and course of illness. For example, response is good in most *B. dermatitidis* infections, but is poor in most diseases caused by *A. fumigatus*. Response is better for skin lesions caused by *B. dermatitidis* than for meningitis due to *C. immitis*; response is better in chronic cryptococcosis than in fulminant candidiasis. Table 1 shows a listing of some systemic mycoses and generally accepted chemotherapeutic agents.

TABLE 1
CHEMOTHERAPEUTIC AGENTS FOR SYSTEMIC MYCOSES

| Disease | First Choice | Second Choice |
| --- | --- | --- |
| Aspergillosis | Amphotericin B | Ketoconazole |
| Blastomycosis | Amphotericin B | Hydroxystilbamidine isethionate |
| Candidiasis | Amphotericin B | Flucytosine or ketoconazole |
| Coccidioidomycosis | Amphotericin B | Ketoconazole |
| Cryptococcosis | Amphotericin B Flucytosine | Either drug alone* |
| Histoplasmosis | Amphotericin B | Ketoconazole* |
| Mucormycosis | Amphotericin B | Miconazole* |

TABLE 1-continued

CHEMOTHERAPEUTIC AGENTS FOR SYSTEMIC MYCOSES

| Disease | First Choice | Second Choice |
|---|---|---|
| Paracoccidioidomycosis | Amphotericin B | Sulfonamides, Ketoconazole* |

*Depending on minimal inhibitory concentration necessary for the fungus.

Infection is the cause of death in 51% of patients with lymphoma and 75% of patients with leukemia. Although bacteria are the causative organisms of many such infections, fungi account for 13% of the fatal infections in patients with lymphoma and for more than 20% of patients with leukemia. The fungus *Candida albicans* causes more than 80% of these infections, and *Aspergillus* spp. is also a frequent cause of such infections. In addition, fungal infection is a major cause of morbidity and mortality in patients with congenital and acquired deficiencies of the immune system. Much concerted effort has been expended in search of agents useful in treating fungal infections of humans. As a result, many compounds have been isolated and shown to have antifungal activity, but problems associated with solubility, stability, absorption, and toxicity have limited the therapeutic value of most of them in human infections. The most useful antifungal antibiotics fall into one of two categories: those that affect fungal cell membranes and those that are taken up by the cell and interrupt vital cellular processes such as RNA, DNA, or protein synthesis. Table 2 lists some useful antifungal agents and their mechanisms of action.

TABLE 2

SOME USEFUL ANTIFUNGAL AGENTS, THEIR CHEMICAL CLASSIFICATION, AND THEIR MECHANISMS OF ACTION

| Class | Compounds | Mechanism |
|---|---|---|
| Polyene | Amphotericin B Nystatin | Interacts with sterols (ergosterol) in fungal cell membrane, rendering cells selectively permeable to the outflow of vital constituents, e.g. potassium |
| Imidazole | Miconazole Clotrimazole Ketoconazole | Inhibits demethylation of lanosterol thus preventing formation of ergosterol, a vital component of fungal cell membrane; also has a direct cidal effect on fungal cells |
| Pyrimidine | 5-Fluorocytosine | Is taken up and deaminated by susceptible cell to form 5-fluorouracil, which in turn inhibits RNA synthesis; also thought to inhibit thymidylate synthetase and DNA synthesis |
| Grisan | Griseofulvin | Binds to tubulin and inhibits microtubule assembly |
| 3-Arylpyrrole | Pyrrolnitrin | Appears to inhibit terminal electron transport between succinate or NADH and coenzyme Q |
| Glutaramide | Cycloheximide | Inhibits protein synthesis at 80S ribosomal level, preventing transfer of aminoacyl tRNA to the ribosome |

The polyene macrolide antibiotics are secondary metabolites produced by various species of Streptomyces. Several common features of these compounds are useful in classifying the more than 80 different polyenes that have been isolated. All are characterized by a macrolide ring, composed of 26–38 carbon atoms and containing a series of unsaturated carbon atoms and hydroxyl groups. These features of the molecule contribute to the polyenes' amphipathic properties (those relating to molecules containing groups with different properties, for example, hydrophilic and hydrophobic). The ring structure is closed by the formation of an internal ester or lactone bond (FIG. 1). The number of conjugated double bonds vary with each polyene, and the compounds are generally classified according to the degree of unsaturation.

Toxic effects of polyene macrolides appear to be dependent on binding to cell membrane sterols. Thus, they bind to membranes of fungus cells as well as to those of other eukaryotic cells (human, plant, and protozoa), but not to bacterial cell membranes, which do not contain membrane sterols. The interaction of polyene macrolides with mammalian and fungal membrane sterols results in transmembrane channels that allow the leakage of intracellular components leading to cell deaths.

The usefulness of an antibiotic is usually measured by the differential sensitivity of the pathogen and host. Two agents, nystatin and amphotericin B, are relatively specific for fungi and have therapeutic usefulness in humans. The relative specificity of these two polyene macrolides is based on their greater avidity for ergosterol, the principal sterol of fungal membranes, compared to cholesterol, the principal sterol of human cell membranes.

Amphotericin B is a heptaene macrolide with seven resonating carbon bonds (see FIG. 1). The compound was first isolated from broth filtrates of *S. nodosum* in 1956. Like other polyene macrolide antibiotics, amphotericin B is insoluble in water. The problem of its solubility has been circumvented by combining the antibiotic with sodium deoxycholate and sodium phosphate and hydrating the mixture with 5% dextrose solution. Amphotericin B is the polyene antibiotic thusfar most sufficiently nontoxic to humans that it has been used parenterally at effective doses against various fungi.

Nystatin, first isolated from *S. noursei*, is structurally related to amphotericin B, but is not classified as a heptaene because the conjugated portion of the ring is interrupted and thus forms a tetraene and a diene (see FIG. 1). Tolerated well both orally and topically, the drug is not available for intravenous use because of its presumed high toxicity and aqueous insolubility. Nystatin is available as oral tablets (500,000 units) or as an ointment for topical use (100,000) units/g). It is used in the management of cutaneous and mucocutaneous candidiasis.

It has recently been shown that the encapsulation of certain drugs in liposomes before administration to the patient can markedly alter the pharmacokinetics, tissue distribution, metabolism and therapeutic efficacy of these compounds. Liposomes may be defined as lipid vesicles which are formed spontaneously on addition of an aqueous solution to a dry lipid film. Further, the distribution and pharmacokinetics of these drugs can be modified by altering the lipid composition, size, charge and membrane fluidity of the liposome in which they are encapsulated.

Recently, liposomes have been used as carriers of Amphotericin B for treatment of murine leishmaniasis (New, R.R.C., et al., "Antileishmanial Activity of Amphotericin and Other Antifungal Agents Entrapped in Liposomes." *J. Antimicrob. Chemother.*, Vol. 8 (1981), pp. 371-381), histoplasmosis (Taylor, R.L., et al., "Amphotericin B in Liposomes: A Novel Therapy for histoplasmosis." *Am. Rev. Respir. Dis.*, Vol. 125 (1982), pp. 610-611), cryptococosis (Graybill, J.R., et al., "Treatment of Murine Cryptococosis with Liposome-Associated Amphotericin B." *J. Infect. Dis.*, Vol. 145 (1982), pp. 748-752). and candidiasis (Tremblay, C., et al., "Comparative Efficacy of Amphotericin B (AMB) and Liposomal AMB (lip-AMB) in Systemic Candidiasis in Mice." *Abstr.* 1983 *ICAAC*, No. 755 (1983), p. 222). Liposome-encapsulated Amphotericin B has also been used for treatment of coccidioidomycosis in the Japanese macaque (Graybill, J.R., et al., "Treatment of Coccidioidomydosis (cocci) in Primates Using Liposome Associated Amphotericin B (Lipo-AMB)." *Abstr.* 1982 *ICCAC*, No. 492 (1982), p. 152).

The present inventors have recently demonstrated that liposome encapsulated amphotericin B (AmpB) may be used to treat experimental murine candidiasis (Lopez-Berestein et al., J. Infect. Dis., Vol. 120, pp 278-283 (1984) and in the treatment of fungal infections in patients with leukemia and lymphoma (Lopez-Berestein et al., J. Infect. Dis., Vol. 151, pp 704-71-(1985).

The treatment of fungal infections remains a major problem in spite of the availability of effective antifungal drugs such as the polyenes. Most of the available polyene antibiotics have toxic side effects that limit their clinical application. Nystatin (Nys), a tetraenediene polyene macrolide antibiotic, has high hydrophobicity, which has precluded its effective systemic administration. It has been used as suspensions prepared in various ways and administered to the patients orally. However, these studies have generally failed to document a beneficial effect of nystatin administration against systemic fungal infections.

SUMMARY OF THE INVENTION

The present invention involves a liposomal agent for treating disseminated fungal infection in an animal. This liposomal agent comprises lipids and the polyene macrolide antifungal compound, nystatin. The nystatin is incorporated in or encapsulated within a liposome for effective therapy of systemic fungal infection.

The liposome in which the nystatin is incorporated is preferably a multilamellar vesicle. The liposome broadly comprises one or more lipids, preferably phospholipids, selected from the group consisting of phosphomonoglyceride, phosphatidic acid and sphingolipid. The lipids are more preferably one or more of phosphatidylcholine, phosphatidylserine, phosphatidylglycerol, sphingomyelin or phosphatidic acid. The lipids are most preferably selected from the group consisting of dimyristoylphosphatidylcholine, dimyristoylphosphatidylglycerol, phosphatidylcholine and phosphatidylglycerol. The liposome of the present invention may comprise a sterol, such as cholesterol.

An important aspect of the present invention involves a method for treating disseminated fungal infection in an animal. This method comprises administering to an animal subject to disseminated fungal infection, a fungicidally effective amount of nystatin encapsulated within a liposome. The liposome is composed as described above. The administering is preferably parenteral in most instances but may be oral or topical if specific colonies of fungus are thereby more directly reached. Parenteral treatment is most useful when the animal is a human suffering from disseminated fungal infection. The method of treatment involves administering a fungicidally effective amount of liposome-incorporated nystatin of between about 1 mg nystatin/kg body weight and about 20 mg nystatin/kg body weight, more preferably between about 2.5 mg nystatin/kg body weight and about 6 mg nystatin/kg body weight. In a most preferred embodiment the treatment method comprises use of liposomes consisting essentially of dimyristoylphosphatidylcholine and dimyristoylphosphatidylglycerol in a ratio of about 7:3 and a nystatin phospholipid ratio of about 1:20.

BRIEF DESCRIPTION OF THE DRAWINGS

FIG. 1 shows chemical structures of amphotericin B and nystatin showing common structural features of macrolide ring with several hydroxyl groups and a conjugated double-bond system. Nystatin differs structurally from amphotericin B in that the conjugated portion of the ring is interrupted to yield a diene and tetraene.

FIG. 2 shows a high-performance liquid chromatograph of nystatin (Lederle). The peak at 10 min corresponds to 3 ug of nystatin.

DETAILED DESCRIPTION OF THE PREFERRED EMBODIMENT

Figure 3:
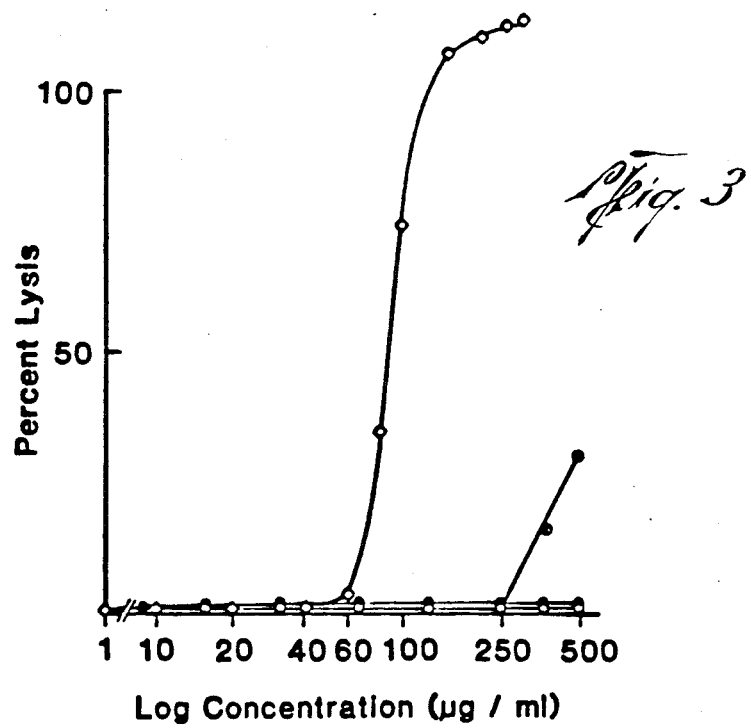
FIG. 3 shows the in vitro toxicity of free-Nys vs. L-Nys to human RBCs. The human RBCs were incubated at 37° C. for 45 min. with (◇) free-Nys, (●) L-Nys, (○) empty liposomes or (⊙) empty liposomes plus free-Nys.

The use of nystatin (Nys) encapsulated in liposomes for the treatment of disseminated fungal infections is described herein as a new effective therapeutic method particularly useful for treatment of systemic or disseminated fungal infections. Liposome-encapsulated nystatin (L-Nys) has a lowered systemic toxicity and an enhanced therapeutic efficiency as compared to free-Nys.

Although free-Nys had antifungal activity in vitro, it was toxic and noneffective when administered intravenously. A reduced in vivo toxicity was observed with L-Nys, while the antifungal properties were maintained. These results were analogous to previous observations with liposomal-Amphotericin B. In vivo, L-Nys was found to be four times less toxic (mean toxic dose (MTD) =16 mg/kg) than the free-Nys (MTD =4 mg/kg) and was non-toxic even when multiple doses were injected (cumulative dose up to 80 mg/kg). L-Nys at 4 mg/kg was effective in improving the survival of mice as compared with the equivalent dose of free-Nys which showed no therapeutic effect in vivo. Further increase in survival time was achieved when higher doses of L-Nys were administered in a multiple dose regimen.

Liposomes have been extensively used to modify the therapeutic index of known active drugs. The observation with most encapsulated drugs has been that the improvement of the therapeutic index was related to reduced toxicity of free-drug after encapsulation. Nystatin, on the other hand, has been shown to be active orally, but its hydrophobic nature has precluded parenteral administration. The observed ineffectiveness of free-Nys as a systemic antifungal may be due to inadequate delivery of the drug to affected sites. Liposome entrapment allowed the systemic administration of Nys, and its use as an active antifungal agent. The present inventors have demonstrated that liposomes enhance the delivery of amphotericin B to infected sites (Lopez-Berestein et al., Cancer Drug Delivery, Vol. 1, pp 199-205 (1986)), thus promoting the drug-drug carrier interactions with systemic fungi.

The most important aspect of the present invention involves liposomes comprising fatty substances such as phospholipids (pl), optionally cholesterol, and nystatin, as well as the preparation and uses of these liposomes. Liposomes of the present invention comprise the nystatin and the phospholipid in a preferred Nys/pl weight ratio between about 0.01/10 and about 0.7/10, a more preferred range being between about 0.02/10 and about 0.08/10. The Nys may be part of the phospholipid lamellae, part of the encapsulated intraliposomal fluid or both.

Preferred phospholipids of these liposomes include phosphatidylglycerol, phosphatidylcholine, sphingomyelin, phosphatidic acid or phosphatidylserine, the more preferred phospholipids being phosphatidylglycerol, phosphatidylcholine or a combination thereof. The most preferred phosphatidylglycerol is one consisting essentially of dimyristoylphosphatidylglycerol and the most preferred phosphatidylcholine is one consisting essentially of dimyristoylphosphatidylcholine. When the liposomes of the present invention comprise dimyristoylphosphatidylglycerol and dimyristoylphosphatidylcholine they are preferably in a ratio between about 1-10 and 10-1, more preferably in a ratio of about 3 to 7.

The liposomes of the present invention may be multilamellar, unilamellar or have an undefined lamellar construction. A pharmaceutical composition comprising the liposomes of the present invention and a pharmaceutically acceptable carrier or diluent may be used for the therapy of disease conditions involving local or systemic fungal infections.

Such liposomes may be administered parenterally, topically or orally, parenterally being preferred for systemic or disseminated fungal infections. Parenteral dosages of L-Nys are generally in fungicidally effect amounts between about 1 mg Nys/kg body weight and about 20 mg Nys/kg body weight are contemplated as adequate in most conditions. The more preferable dose range is between about 2.5 mg/kg and about 6 mg/kg.

The particular dosages, if an infected human is being treated may vary in each case according to the condition of the patient, the type and extent of fungal infection and directions of an attending physician.

A focal point of the present invention involves a method of treating a host animal afflicted with a fungal infection. This method comprises administering to the host an amount of a liposome of the present invention comprising a phospholipid and a fungus-inhibiting effective amount of nystatin. The administering step is preferably parenteral and by intravenous, intraarterial, intramuscular, intralymphatic, intraperitoneal, subcutaneous, intrapleural or intrathecal injection or by topical application or oral dosage. Such administration is preferably repeated on a timed schedule, for example twice daily for a period of two weeks. The treatment may be maintained until the fungus has been eliminated and may be used in conjunction with other forms of antifungal therapy or support therapy. Such parenteral administration preferably involves L-Nys suspensions in pharmaceutically acceptable solutions such as sterile isotonic aqueous solutions. These suspensions may be obtained fully prepared or may be prepared from preformed components. As known to those skilled in the art, L-Nys may be prepared and mixed with pharmaceutically acceptable solutions to form suspensions for parenteral administration.

Topical administration of L-Nys may involve pharmaceutical compositions such as suspensions, creams or ointments which may be obtained fully prepared or prepared from L-Nys precursors such as pellets. Such topical administration may be near to sites of localized fungal infection such as the epithelium or mucosa for example. Although Nys has been topically used, L-Nys should more effectively inhibit fungal proliferation.

Oral administrations of L-Nys preferably involve encapsulation of L-Nys whereby the L-Nys is protected from much gastric and intestinal digestive activities before release from encapsulation.

The methods of preparation of L-Nys and chemotherapeutic treatment therewith described in the Examples contained later herein are readily adapted to the production and use of analogously described liposomes by simple substitutions of appropriate lipids or methods.

Liposomes containing Nys described herein may be prepared from various amphipathic substances including natural or synthetic phospholipids. The phospholipids usable to produce liposomes are numerous and not exhaustively listed herein since they are generally well known in the art. These phospholipids include but are not limited to: lecithin, phosphatidylethanolamine, lysolecithin, lysophatidylethanolamine, phosphatidylserine, phosphatidylinositol, sphingomyelin, cardiolipin, phosphatidic acid and the cerebrosides. Most preferable phospholipids for the practice of aspects of the present invention include dimyristoylphosphatidylglycerol (DMPG) and dimyristoylphosphatidylcholine (DMPC). A sterol such as cholesterol in proportions ranging from less than 1% to about 50% may be included with phospholipids and nystatin to produce liposomes of the present invention. A preferable but not limiting combination of DMPG and DMPC has been found to be ratio of 3 to 7 although ratios between 1:10 and 10:1 are contemplated as satisfactory.

Either unilamellar or multilamellar or other nystatin-containing liposomes may be used in the practice of the present invention. Multimellar liposomes are presently preferred since the Nys of the present invention is substantially water-insoluble. Nys appears to be incorporated into the phospholipid bilayers of the liposome lamellae.

The liposome-encapsulated nystatin of the present invention also may prove useful in the prophylaxis and/or treatment of disease caused by human T lymphotropic retrovirus, designated HTLV-III/LAV. As Gallo recently pointed out, HTLV-III/LAV may be carried in vivo by monocytes and macrophages (at p 51, Scientific American, January, 1987 pp 47–56). These cell types may thus serve as potentially infectious and deadly HTLV-III/LAV reservoirs.

In a recently published study, Schaffner et al. (Biochem. Pharmacol., V 35, pp 4110-4113 (1986)) showed data indicating that the replication of HTLV-III/LAV in the monocyte-related cell line H9 was inhibited by several antifungal polyene macrolides. These polyene macrolides included amphotericin B and amphotericin B methyl ester ascorbate.

The phagocytes of the blood—monocytes, macrophages and polymorphonuclear leukocytes—haracteristically bind and ingest foreign substances, even prior to an immune response. These phagocytes also are among the first cells to take up circulating liposomes. It appears likely that parenteral administration to an animal of liposomes comprising a polyene macrolide such as nystatin, for example, should be useful to inhibit intracellular HTLV-III/LAV proliferation. The liposome-induced increased bioactivity of nystatin may prove important in the control of disease caused by HTLV-III/LAV infection.

These following examples are presented to describe preferred embodiments and utilities of the present invention but are not meant to limit the present invention unless otherwise stated in the claims appended hereto. For example, although dimyristoylphosphatidylcholine and dimyristoylphosphatidylcholine were used to form liposomes, these particular lipid forms are by no means the only available usable lipids known to those skilled in the art. Nor do the particular formation methods for or types of liposomes used in these examples represent the only usable methods or liposome types.

EXAMPLE 1

Drug, Lipids and Reagents

Nystatin (bulk powder) was obtained from Lederle Laboratories (Pearl River, N.Y.). Chromatographically pure dimyristoylphosphatidylcholine (DMPC) and dimyristoylphosphatidylglycerol (DMPG) were purchased from Avanti Polar Lipids (Birmingham, Ala.). Methanol for high-performance liquid chromatography (HPLC), dimethyl sulfoxide (DMSO), and N,N-dimethylformamide (DMFA) were purchased from Fisher Scientific (Fair Lawn, N.J.). Human AB serum was from MA Bioproducts (Walkersville, Md.) Human RBCs were obtained from normal volunteers.

EXAMPLE 2

Nystatin Characterization

The high-performance liquid chromatography of Nys (HPLC) was performed with a system consisting of Water M6000A and M45 solvent delivery systems, with U6K Universal LC injector, Waters Automated gradient controller and programmer, a model 441 fixed wavelength absorbance detector, and Houston Instruments' Omniscribe recorder. Waters u-bondapak C-18 reverse-phase column (0.45 mm × 30 cm) was used for the analysis. The mobile phase consisted of methanol:water (70:30) pumped at a flow rate of 2 ml/min, and the eluant was monitored for absorbance at 280 nm, 0.02 AUFS. The purity was calculated as percent peak area corresponding to Nys, divided by peak areas of total number of peaks in each chromatogram.

Nystatin (Lederle) was soluble in methanol (1 mg/ml), DMFA (15 mg/ml) and DMSO (40 mg/ml). A typical chromatograph of HPLC analysis of Nys is shown in FIG. 2. Optimal separation of the drug was achieved using 70% (vol/vol) methanol as the mobile phase and other conditions as specified. The retention time of Nys was 10 min and the purity calculated was 72%.

EXAMPLE 3

Liposome Preparation and Standardization

Multilamllar vesicles (MLV) were prepared as described previously (Lopez-Berestein et al., J. Infect. Dis., Vol. 120, pp 278–283 (1984). Nystatin was solubilized in methanol (1 mg/ml) and stored at 4° C., protected from light. Phospholipids, DMPC:DMPG (7:3), at a constant amount, were mixed with increasing amounts of the drug and the organic solvents evaporated under vacuum using a rotary evaporator. The dried lipid-drug film was suspended in phosphate-buffered saline (PBS) and handshaken, allowing the film to form liposomes. The suspensions were then recovered from the flasks and centrifuged at 20,000 rpm for 1 hr. The pellets were resuspended in PBS and Nys incorporated in liposomes was determined by absorbance at 306 nm. Similarly, liposomes composed of phospholipids and sterols at a ratio of 9:1 were also prepared. The stability of Nys liposomes was assessed by incubating equal amounts of L-Nys with PBS and human AB serum at 37° C. At indicated time intervals, samples were taken out, centrifuged at 10,000 × g for 15 min and Nys concentration in the pellet was measured.

EXAMPLE 4

Encapsulation Efficiency of Nystatin in Liposomes

The encapsulation efficiencies of different batches of liposomes prepared with a fixed amount of phospholipid and increasing doses of Nys are presented in Table 3. The maximum incorporation was obtained at 600 ug Nys/10 mg phospholipid (drug/phospholipid ratio =1:16.7) and decreased thereafter.

TABLE 3

| Encapsulation efficiency of Nystatin in liposomes | | | |
|---|---|---|---|
| Drug (ug/10 mg pl) | Drug/pl[b] ratio | ug Drug incorporated in MLV per (10 mg PL) | Encapsulation efficiency[c] |
| 10 | 1:1000 | 10 | 100 |
| 20 | 1:500 | 20 | 100 |
| 40 | 1:250 | 40 | 100 |
| 60 | 1:167 | 60 | 100 |
| 80 | 1:125 | 80 | 100 |
| 100 | 1:100 | 95 | 95 |
| 200 | 1:50 | 180 | 90 |
| 400 | 1:25 | 400 | 100 |
| 600 | 1:16.7 | 600 | 100 |
| 800 | 1:12.5 | 640 | 80 |
| 1000 | 1:10 | 628 | 62.8 |

[a]Liposomes were multilamellar vesicles (MLV) composed of dimyristoylphosphatidylcholine (DMPC) and dimyristoylphosphatidylglycerol (DMPG) in a molar ration of 7:3.
[b]pl is total phospholipid consisting of both DMPC and DMPG.
[c]Percent of drug encapsulated in MLV (the pellet)/total drug added. The Nystatin content was measured by absorbance of aliquots, dissolved in methanol., at 306 nm.

EXAMPLE 5

Stability of Liposome-incorporated Nystatin (L-Nys)

Liposomes containing 500 ug Nys/10 mg of phospholipid were prepared, as described in Example 4, divided into equal aliquots, and incubated with PBS or human AB serum for various time intervals. The amount of drug recovered in a centrifuged pellet after incubation for each time point is shown in Table 4. Liposomes, which were stable up to 72 hr in PBS and were stable up to 24 hr in serum, but only 30% of the drug was recovered in the pellet after a 72-hr incubation.

TABLE 4

Stability profile of Nystatin liposomes at 37° C.

| Incubation time (hr) | % Nystatin retained in pellet[a] | |
|---|---|---|
| | PBS[b] | Serum[c] |
| 1 | 100 | 100 |
| 2 | 100 | 95 |
| 4 | 100 | 75 |
| 24 | 100 | 65 |
| 48 | 100 | — |
| 72 | 100 | 30 |
| 168 | 50–70 | — |

[a]The values are % of Nystatin recovered in samples as compared with identical samples at 0 hr taken as 100% controls.
[b]PBS is phosphate buffered saline.
[c]Serum used was human AB serum.

EXAMPLE 6

In vitro fungal inhibition

Organism, culture, and assay of antifungal activity in vitro. All strains of yeast were grown overnight at 37° C. on Sabouraud dextrose agar (SDA) plates. All molds were grown at 30° C. on SDA for 3 to 10 days prior to collection of spores. The inoculum was then processed for susceptibility testing as described earlier (Hopfer et al., Antimicrob. Agents Chemotherap., Vol. 25, pp 387–389 (1984)). A twofold serial dilution method (Shadomy et al., In E. H. Lennette, et al., (eds.) Manual of Clinical Microbiology, 3rd ed. American Society for Microbiology, Washington, D.C., pp. 647–653 (1980)) adapted to microtiter plates was used to determine the minimal inhibitory concentration (MIC) of the drugs. The MIC of L-Nys were compared with that of free-Nys. Empty liposomes and 5% dimethylsulfoxide (DMSO) were used as controls.

The MIC of free- or L-Nys for *C. albicans* strain 336 is shown in Table 5. The antifungal activity was maintained after Nys was entrapped in liposomes with or without sterols. Empty liposomes and DMSO at concentrations equivalent to those used with drug samples did not inhibit growth.

TABLE 5

Antifungal activity of free nystatin vs. liposomal-nystatin in vitro

| Drug | Minimal inhibitory concentration[a] (ug/ml) |
|---|---|
| Free nystatin[b] | 1.0 |
| Liposomal nystatin | |
| PL[c] | 1.0 |
| PL:C[d] | 1.0 |
| PL:E[e] | 2.0 |
| DMSO | Nil |
| Empty liposomes[f] | Nil |

[a]Minimal inhibitory concentration was determined against *Candida albicans* strain 336.
[b]Free nystatin was dissolved in DMSO and diluted further with saline, which contained 5% DMSO at 1 mg/ml concentration.
[c]Phospholipids (DMPC:DMPG, 7:3) only used to prepare liposomes.
[d]Liposomes contained phospholipids and cholesterol at a ration of 9:1.
[e]Liposomes were composed of phospholipids and ergosterol at a ratio of 9:1.
[f]DMSO and empty liposomes at an equivalent dose were similarly diluted as free- or Liposomal nystatin.

As shown in Table 6, the minimal inhibitory concentration (MIC) of liposomal nystatin (L-Nys), as compared to that of free nystatin, is usually significantly lower. The L-Nys was surprisingly effective as an antifungal toxin for a wide variety of fungi. The L-Nys was prepared and tested generally as described above in this and earlier examples, except for the various new fungal varieties. In contrast, previous analogous results with free amphotericin B and liposome-encapsulated amphotericin B has indicated either an approximate toxic equivalence or that the encapsulation decreased amphotericin toxicity to fungi. (Hopfer et al., Antibacterial Agents and Chemotherapy, Vol. 25, No. 3, pp. 387–389 (1984)).

TABLE 6

In Vitro Antifungal Spectrum of Free-and Liposomal-Nystatin

| Fungal strains | Minimal Inhibitory Concentration (ug/ml) | |
|---|---|---|
| | Free-Nystatin | Liposomal-Nystatin |
| *Candida albicans* | | |
| #1 | 2 | 2 |
| #2 | 2 | 1 |
| #3 | 4 | 2 |
| #4 | 4 | 2 |
| #5 | 8 | 2 |
| #6 | 4 | 2 |
| #7 | 8 | 2 |
| #8 | 8 | 2 |
| #9 | 4 | 2 |
| #10 | 4 | 2 |
| *Candida tropicalis* | | |
| #1 | 16 | 8 |
| #2 | 8 | 2 |
| #3 | 4 | 2 |
| #4 | 4 | 2 |
| *Candida paratropicalis* | | |
| #1 | 2 | 2 |
| #2 | 2 | 2 |
| #3 | 4 | 2 |
| #4 | 4 | 2 |
| *Torulopsis globrata* | | |
| #1 | 4 | 2 |
| #2 | 2 | 2 |
| #3 | 4 | 2 |
| #4 | 4 | 2 |
| *Cryptococcus neoformans* | | |
| #1 | 4 | 2 |
| #2 | 4 | 2 |
| *Aspergillus not fumigatus* | | |
| #1 | 4 | 1 |
| #2 | 16 | 8 |
| *Aspergillus fumigatus* | 8 | 8 |
| Curvularia | 2 | 0.5 |
| *Aspergillus niger* | 4 | 2 |
| *Aspergillus flavus* | 1 | 0.5 |
| Fusarium | 62.5 | 62.5 |
| Rhizopus | 4 | 4 |
| Mucor | 2 | 1 |
| Alternaria | 2 | 1 |

TABLE 6-continued

| In Vitro Antifungal Spectrum of Free-and Liposomal-Nystatin | | |
|---|---|---|
| Fungal strains | Minimal Inhibitory Concentration (ug/ml) | |
| | Free-Nystatin | Liposomal-Nystatin |
| Allescheria | 16 | 16 |

EXAMPLE 7

Toxicity of Free Nys and L-Nys to human RBC's in vitro

Lysis of human red blood cells (RBCs) was quantitated by measuring the release of hemoglobin in the supernatants at 550 nm, as described previously (Mehta et al., Biochem. Biophys, Acta., Vol. 770, pp. 230–234 (1984)). Various doses of L-Nys were incubated with fresh washed human RBCs at 37° C for 45 min. Free-Nys, dissolved in dimethyl formamide (DMFA), was added to the assay at a 3% final solvent concentration. Appropriate solvent controls, empty liposomes, and empty liposomes plus free-drug were also included in each experiment. Release of hemoglobin by hypotonic lysis of the same number of human RBCs by water was taken as 100% positive control, while cells treated with PBS were taken as negative controls.

A linear increase in lysis of human RBCs were observed with free-Nys ranging from 60 to 120 ug/ml, with 100% lysis produced at 120 ug/ml (FIG. 3). In contrast, L-Nys did not cause any lysis with doses up to 500 ug/ml. Empty liposomes alone did not affect the human RBCs and, to some extent, they protected against the effect of free-Nys. A 375 ug/ml dose of free-Nys with empty liposomes produced only 15% lysis, while a 30% lysis was observed with 500 ug/ml of free-Nys when present with empty liposomes. Dimethylformamide at concentrations equivalent to those used with free-Nys did not affect human RBCs.

EXAMPLE 8

In vivo Toxicology of Nys and L-Nys

Groups of eight Hale-Stoner mice (6–8 weeks old, body wt=20–25 g; Univ. of TX Science Park, Bastrop, TX) each were injected with various doses of free-Nys (in 5% DMSO diluted with saline), L-Nys, empty liposomes or 5% DMSO as control. The mice were observed for acute, subacute, and chronic toxicity and the survival time of each animal in different groups was noted. After 45 days, the surviving animals were sacrificed and blood and tissue samples were obtained. Blood biochemistry examination included blood urea nitrogen, alkaline phosphatase, and lactic dehydrogenase (LDH). The organs (liver, spleen, lungs and kidneys) were obtained and preserved in 10% formalin. Tissue slices were processed for hematoxylin-eosin and Gomori methenamine silver stains.

Figure 4:
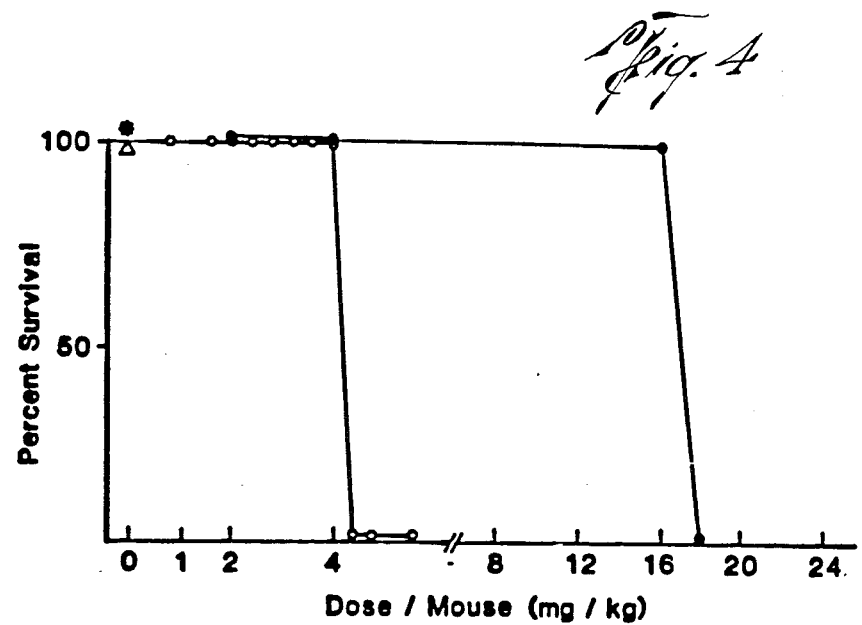
FIG. 4 shows the acute toxicity of free-Nys vs. L-Nys in vivo. The mice were injected (iv) with (○) free-Nys, (●) L-Nys, (△) 5% DMSO or (*) empty liposomes. The total lipid dose was 400 mg/kg/mouse.

The maximal tolerated dose (MTD) of free-Nys was 4 mg/kg body weight and at a dose of 4.4 mg/kg, all the animals died immediately (FIG. 4, free Nys=(○); L-Nys =(○). Liposomal-Nys, on the other hand, showed a maximum tolerated dose of 16 mg nystatin/kg body weight. Empty liposomes (400 mg/kg) and DMSO equivalent to the highest dose of free-Nys did not show any toxic effects and the animals survived until the experiment was terminated (i.e., 45 days). No subacute or chronic toxic reactions were observed in the surviving animals. No significant changes in the blood biochemistry pattern were observed. Histopathology studies failed to demonstrate the cause of death in these animals.

EXAMPLE 9

Figure 5:
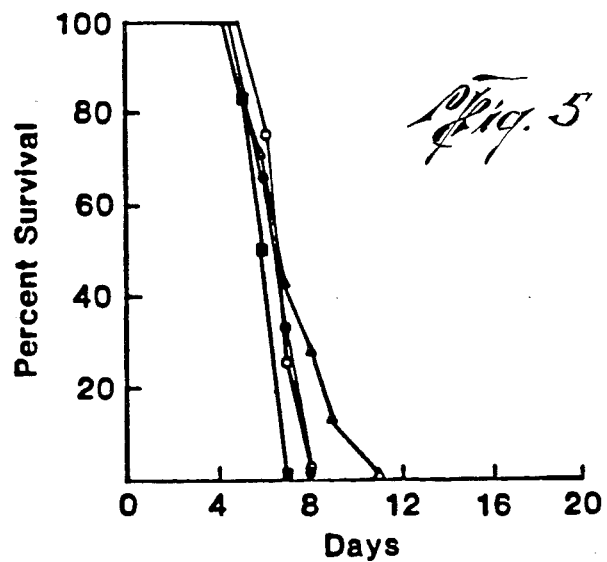
FIG. 5 shows the antifungal activity of free-Nys in mice. Two days after receiving infection with *C. albicans*, mice were injected (iv) with (●) no drug, or free-Nys at doses (△) 1 mg/kg, (■) 2 mg/kg, (○) 4 mg/kg.

Therapy with a single dose of free Nys for disseminated fungal infection by Candida albicans Hale-Stoner mice, six to eight weeks old (body weight, 20–25 g) were purchased from The University of Texas Science Park (Bastrop, TX). The mice (eight per group) were injected with 0.2 ml of C. albicans cell suspension containing $7 \times 10^5$ colony-forming units (cfu) via the tail vein. This concentration of cells was consistent in producing a disseminated infection after 48 hr, affecting liver, spleen, lungs, and kidneys primarily. Infected mice were treated with increasing doses of free-Nys, ranging from 1 mg to 4 mg/kg body weight (FIG. 5). None of the doses tested improved the survival of infected mice as compared to the control untreated group. Five percent DMSO did not affect the survival of mice.

EXAMPLE 10

Therapy with Single Doses of Free Nys or L-Nys for Disseminated Fungal Infections with Candida albicans Mice were infected with C. albicans as described in Example 9. Groups of eight mice each were injected (iv) with various doses of free-Nys, L-Nys, empty liposomes or 5% DMSO two days after the injection of C. albicans. The survival of the animals in each group was noted and compared with that of the untreated control group.

Figure 6:
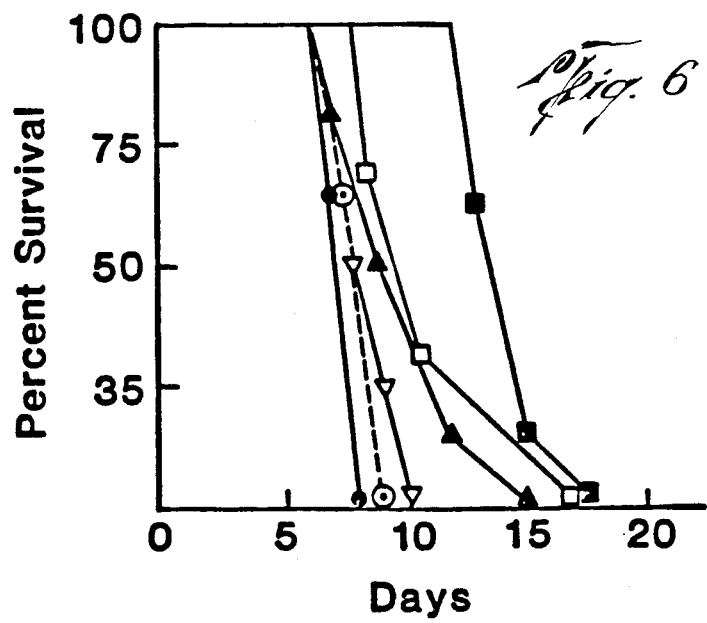
FIG. 6 shows the effect of liposome encapsulation on the antifungal activity of Nys in mice; single-dose treatment. Two days after challenge with *C. albicans*, the animals were treated with (●) no drug, (⊙) free-Nys (4 mg/kg) or L-Nys at doses (▼) 2 mg/kg, (△) 4 mg/kg, (□) 8 mg/kg, and (■) 12 mg/kg.

Groups of mice were treated with various doses of L-Nys (range, 2–12 mg/kg), free-Nys (1–4 mg/kg), empty liposomes (400 mg of lipid/kg) (FIG. 6). Empty liposomes did not show any effect on the survival of mice. No difference in survival of mice was observed with a 2 mg/kg dose of L-Nys as compared with free-Nys, whereas doses of 4 mg/kg and 8 mg/kg showed improvement in survival (P less than 0.01 and less than 0.02, respectively). Furthermore, a dose of 12 mg/kg showed a significant improvement in survival (P less than 0.003) when compared with MTD of free-Nys. However, all mice died within 18 days, regardless of treatment.

EXAMPLE 11

Therapy with Multiple Doses of Nys or L-Nys for Disseminated Fungal Infections with C. albicans Two days after the injection of C. albicans (iv), (as described in Examples 9 and 10), the mice were treated with different doses of free-Nys, L-Nys, empty liposomes or 5% DMSO control for five consecutive days. The multiple-dose groups were also compared with appropriate cumulative single doses (see Example 10). The animals were then observed for survival or any toxicity pertaining to the treatment with five daily doses.

These experiments were terminated at 60 days, and blood and tissue samples were collected from the surviving animals after sacrifice.

Survival curves were calculated by the method of Kaplan and Meier (J. Amer. Stat. Assoc., Vol. 53, pp 457–462 (1953)) and tests for differences in survival distributions were based on a generalized Wilcoxon test (Gehan., Biometrika, Vol. 52, pp 203–223 (1965)). Linear trend and $X^2$ test for differences in response rates among the groups and paired t-tests were used to compare the means.

Figure 7:
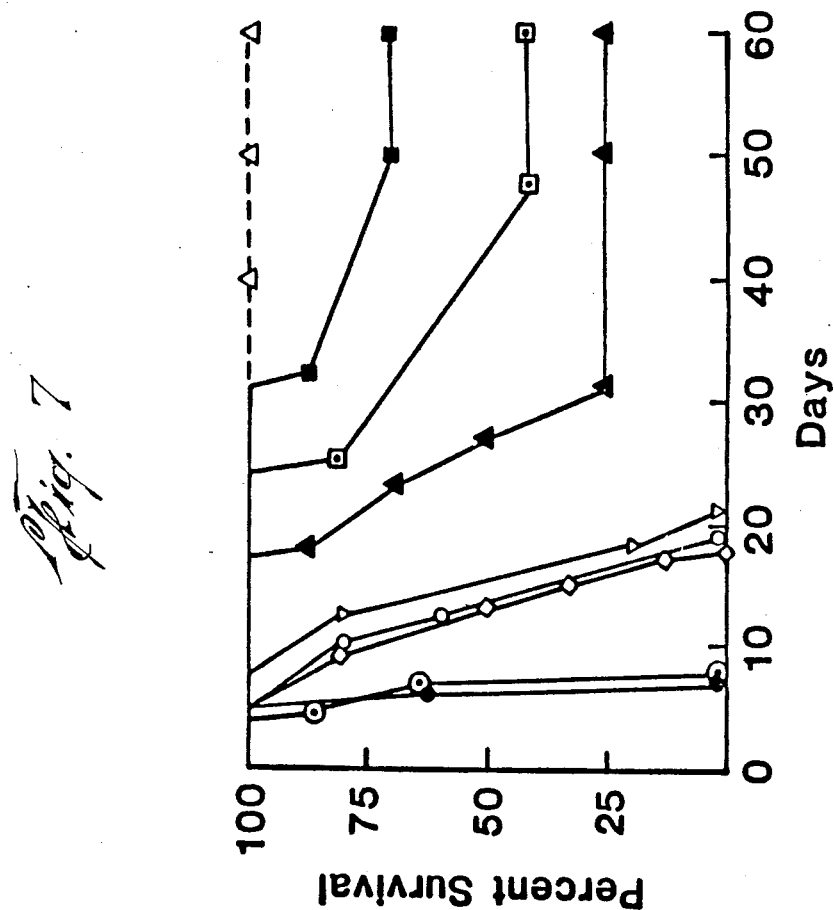
FIG. 7 shows the effect of L-Nys on the survival of mice infected with *C. albicans*; multiple-dose treatment. The animals were treated with (●) no drug, (⊙) free-Nys (4 mg/kg×5) or L-Nys in single dose of (○) 12 mg/kg, (△) 16 mg/kg and multiple doses of (◇) 2.4 mg/kg×5, (▲) 6 mg/kg×5, (□) 8 mg/kg×5, (■) 12 mg/kg×5, (--△) 16 mg/kg×5.

Groups of mice were injected with indicated doses of free-Nys (MTD) and L-Nys for five consecutive days. These multiple doses were compared with MTDs of free- or L-Nys given as single doses. The experiments also included groups of animals injected with the daily equivalent dose of empty liposomes or 5% DMSO, injected on five consecutive days, as well as the untreated controls (FIG. 7). The animals in all the groups treated with single or multiple doses of free-Nys died as rapidly as the untreated controls. L-Nys, on the other hand, produced significant improvement in the survival of mice. The 12 mg/kg dose given as a single or divided dose (2.4 mg×5) also showed a similar pattern of survival; a significant improvement over the groups treated with free drug was observed (P less than 0.003). When given five times, the 12 mg/kg dose (total dose =60 mg/kg) produced a dramatic increase in survival (P less than 0.007), with 70% of the mice surviving at day 60, as compared with a survival time of 18 days and 10 days in case of treatments with single dose of L-Nys and single or multiple doses of free-Nys, respectively. The medium-cumulative dose (6 mg Nys×5) also showed a marked improvement in survival (P less than 0.001). The increase in survival time was proportional to the total dose of the liposomal-drug. The mice could also tolerate a dose of 16 mg Nys/kg body weight for five days (a total of 80 mg Nys/kg), but only when it was given at a slow rate. This dose showed a 100% survival of mice for up to 60 days when the experiment was terminated.

Changes may be made in the elements and methods described herein or in the steps or the sequence of steps of the method described herein without departing from the concept and scope of the invention as defined in the following claims.

What is claimed is:

1. A method for treating systemic fungal infection in an animal comprising parenterally administering to said animal a fungicidally effective amount of a multilamellar liposome comprising nystatin one or more phospholipid.

2. The method of claim 1 wherein the liposome further comprises 1 to 50% of a sterol.

3. The method of claim 1 wherein the phospholipid is one or more of phosphomonoglyceride, phosphatidic acid and sphingolipid.

4. The method of claim 1 wherein the phospholipid is one or more of phosphatidylcholine, phosphatidylserine, phosphatidylglycerol, sphingomyelin and phosphatidic acid.

5. The method of claim 1 wherein the phospholipid is one or more of dimyristoylphosphatidylcholine, dimyristoylphosphatidylglycerol, phosphatidylcholine and phosphatidylglycerol.

6. The method of claim 1 wherein the animal is a human.

7. The method of claim 1 wherein the fungicidally effective amount is between about 1 mg nystatin/kg body weight and about 20 mg nystatin/kg body weight.

8. The method of claim 1 wherein the fungicidally effective amount is between about 2.5 mg nystatin/kg body weight and about 6 mg nystatin/kg body weight.

9. The method of claim 1 wherein the phospholipid consist essentially of dimyristoylphosphatidylcholine and dimyristoylphosphatidylglycerol.

10. The method of claim 1 wherein the phospholipids consist essentially of dimyristoylphosphatidylcholine and dimyristoylphosphatidylglycerol in a ratio of about 7 to 3.

11. The method of claim 1 wherein the administration is intravenous, intraarterial, subcutaneous, intramuscular, intralymphatic, intraperitoneal or intrapleural.

12. The method of claim 1 wherein the nystatin and phospholipids have a weight ratio between about 0.01/10 and about 0.7/10.

13. The method of claim 12 wherein the weight ratio is between about 0.02/10 and about 0.08/10.

* * * * *

UNITED STATES PATENT AND TRADEMARK OFFICE
CERTIFICATE OF CORRECTION

PATENT NO. : 4,812,312
DATED : March 14, 1989
INVENTOR(S) : Lopez-Berestein, et al.

It is certified that error appears in the above—identified patent and that said Letters Patent is hereby corrected as shown below:

On the title page assignee should read Assignee [73], 'Board of Regents of the University of Texas System, Austin, Tex.' should be "Board of Regents, The University of Texas System, Austin, Tex."

Claim 1, (column 16, line 2), add the word "and" between the word 'nystatin' and the word 'one'

Claim 9, (column 16, line 26), change the word 'consist' with the word "consists"

Claim 10, (column 16, line 28), change the word 'phospholipids' to "phospholipid"

Claim 10, (column 16, line 29), change the word 'consist' to "consists"

Claim 12, (column 16, line 36), change the word "phospholipids" to "phospholipid"

UNITED STATES PATENT AND TRADEMARK OFFICE
CERTIFICATE OF CORRECTION

PATENT NO. : 4,812,312

DATED : March 14, 1989

INVENTOR(S) : Lopez-Berestein, et al

It is certified that error appears in the above-identified patent and that said Letters Patent is hereby corrected as shown below:

In Figure 1, except for that in the term '$NH_2$', change every 'N' to and "H".

Signed and Sealed this

Twenty-fourth Day of October, 1989

Attest:

DONALD J. QUIGG

Attesting Officer

Commissioner of Patents and Trademarks